United States Patent [19]

Sapiejewski

[11] Patent Number: 4,856,118
[45] Date of Patent: Aug. 15, 1989

[54] HEADPHONE CUSHIONING

[75] Inventor: Roman Sapiejewski, Boston, Mass.

[73] Assignee: Bose Corporation, Framingham, Mass.

[21] Appl. No.: 13,339

[22] Filed: Feb. 11, 1987

[51] Int. Cl.4 .............................................. A42B 1/06
[52] U.S. Cl. ........................................ 2/209; 381/183; 181/129
[58] Field of Search ................. 381/183, 187, 138, 72, 381/74; 2/209; 181/129; 5/449, 451

[56] References Cited

U.S. PATENT DOCUMENTS

| | | | |
|---|---|---|---|
| 2,989,598 | 6/1961 | Touger et al. | 381/187 X |
| 3,051,961 | 9/1962 | Clark | 2/209 |
| 3,052,887 | 9/1962 | Sockel et al. | 2/209 |
| 3,073,410 | 1/1963 | Gongoll | 2/209 |
| 3,391,407 | 7/1968 | Waters | 2/171.3 |
| 3,862,451 | 1/1975 | Miller et al. | 2/209 |
| 3,908,200 | 9/1975 | Lundin | 2/209 |
| 4,456,642 | 6/1984 | Burgdörfer et al. | 5/449 |
| 4,572,323 | 2/1986 | Randall | 2/209 |
| 4,674,134 | 6/1987 | Lundin | 2/209 |

FOREIGN PATENT DOCUMENTS 0170947  2/1986  European Pat. Off. ............... 5/451

Primary Examiner—Ronald Feldbaum
Attorney, Agent, or Firm—Charles Hieken

[57] ABSTRACT

A headphone cushion comprises two concentric rings of nonliquid gelatin-like silicone on a layer of soft, slow recovery foam enclosed in a thin stretchable layer of polyurethane skin.

11 Claims, 1 Drawing Sheet

HEADPHONE CUSHIONING

The present invention relates in general to headphone cushioning and more particularly concerns novel apparatus and techniques for providing a headphone cushion that provides a good acoustic seal between a headphone cup and the head and ear of a wearer while being relatively lightweight and comfortable to wear.

For background reference is made to U.S. Pat. No. 4,455,675 and application Ser. No. 06/749,575 filed June 27, 1985, entitled HEADPHONE WITH SOUND PRESSURE SENSING MEANS, now U.S. Pat. No. 4,644,581, incorporated herein by reference.

Those patents describe a headphone system for reducing noise and producing a relatively uniform frequency response that does not vary appreciably among users while reducing distortion. Those inventions use relatively compact headphones that may be worn comfortably without excessive pressure on the head from forces urging the cups against the head and achieving noise reduction while faithfully reproducing a music or speech signal. The present invention embodies an improved headphone cushion that further improves comfort while providing a good acoustic seal.

According to the invention, the headphone cushion comprises at least one ring of nonliquid gelatin-like material on a ring of soft, slow recovery foam enclosed within a thin stretchable layer of polyurethane skin. Unlike a liquid which flows and is relatively incompressible, the nonliquid gelatin-like material is compressible and does not flow. Preferably, there are two concentric rings separated by a groove therebetween.

Numerous other features, objects and advantages of the invention will become apparent from the following specification when read in connection with the accompanying drawing in which.

Figure 1:
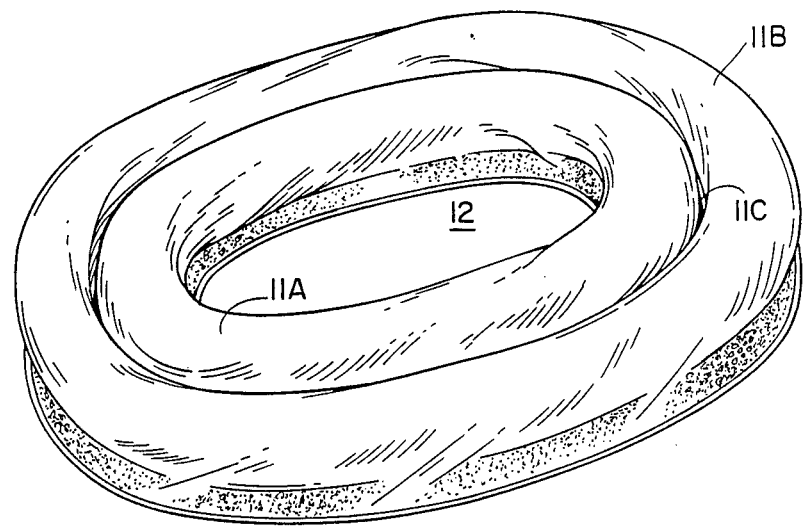
FIG. 1 is a perspective view of an embodiment of the invention.
Figure 2:
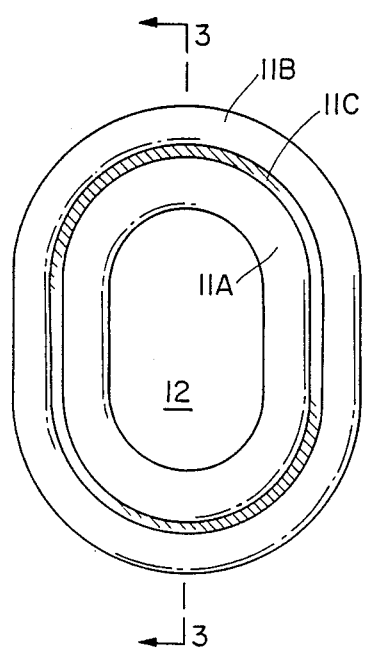
FIG. 2 is an inside plan view of the cushion of FIG. 1.

With reference now to the drawing and more particularly FIG. 1 thereof, there is shown a perspective view of a headphone cushion 11 according to the invention. Cushion 11 has an inner ring 11A surrounded by a concentric outer ring 11B, both surrounding an opening 12 through which sound is transmitted from the headphone transducer (not shown) to the ear of the wearer. FIG. 2 is an inside plan view of headphone cushion 11 showing the face contacting the head.

Figure 3:
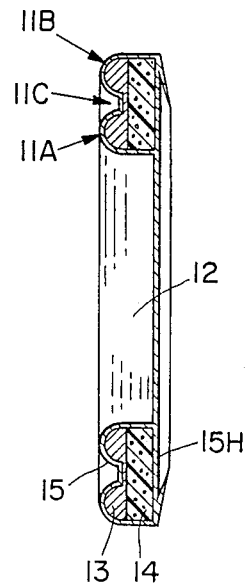
FIG. 3 is a view through section 3—3 of FIG. 2.
Figure 4:
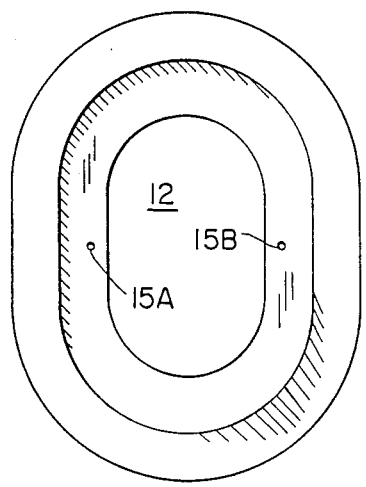
FIG. 4 is an outside plan view of the cushion of FIG. 1.

Referring to FIG. 3, there is shown a sectional view through section 3—3 of FIG. 2. The structure includes a nonliquid gelatin-like silicone layer 13 resting on a layer of soft, slow recovery foam 14, such as Speciality Composites Inc. C40 of 6 lbs/cu. ft. density. Foam layer 14 and silicone layer 13 are enclosed by a thin stretchable layer of poyurethane skin 15, typically of thickness 5 mils or less. The headphone side 15H of layer 15 is formed with two small venting openings 15A and 15B visible in the outside plan view of FIG. 4 showing the face away from the head. The silicone side of film 15 rests against the head. To provide more compliance and better seal to the head, only the outer ring should be supported by the rigid structure of the ear cup, the inner ring being allowed to float.

The combination of silicone layer 13 and foam layer 14 coact to provide an extremely comfortable fit for the wearer while providing a good acoustic seal, good damping and being relatively light in weight. The slow recovery foam and the vent openings 15A and 15B provide for a slow recovery effect when headphones are removed and the cushion expands. The vents also allow for pressure equalization. A relatively fast recovery effect is disadvantageous because it produces an annoying effect on the eardrum of the listener, analogous to operating a plumber's helper around the ear.

In a specific embodiment of the invention silicone gel 11 was RTV silicone gel (penetration 5 mm. of Universal Penetrometer 19.5 6 m. shaft, 6.3 mm. dia.), the maximum width of the cushion along the diameter embracing openings 15A and 15B was 3.75", the maximum height along section 3.3 was 4.75", the radial width spanned by rings 11A and 11C was 1.0", the thickness of the assembly including rings 11A and 11B and film layer 14 was 0.62", that across slicone layer 13 0.22" and the depth of recess 11C 0.16". Openings 15A and 15B were 0.06" diameter through the outer skin only the separation between openings 15A and 15B was 2.00", each being 1.00" from the center.

There has been described novel apparatus and techniques for appreciably improving the comfort to a wearer of headphones while providing a good acoustic seal. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A headphone cushion comprising,
   at least one ring of compressible nonliquid silicone gel material that behaves like an elastic solid capable without perminent loss of size, or shape and that does not flow on a layer of foam material,
   and a thin stretchable skin enclosing said ring and layer of foam material
   said ring and foam layer coacting to provide a comfortable fit for the wearer of said cushion while providing a good acoustic seal.

2. A headphone cushion in accordance with claim 1 wherein said foam material is soft, slow recovery foam.

3. A headphone cushion in accordance with claim 1 wherein said skin is polyurethane.

4. A headphone cushion in accordance with claim 2 wherein said skin is polyurethane.

5. A headphone cushion in accordance with clam 1 wherein said thin stretchable skin is formed with at least one vent opening for allowing pressure equalization and coacting with said foam material for providing a slow recovery effect when headphones are removed and said cushion expands.

6. A headphone cushion in accordance with claim 2 wherein said thin stretchable skin is formed with at least one vent opening for allowing pressure equalization and coacting with said foam material for providing a slow recovery effect when headphones are removed and said cushion expands.

7. A headphone cushion in accordance with claim 5 and further comprising at least a second of said openings, said openings being located on a diameter of said ring.

8. A headphone cushion in accordance with claim 7 and further comprising at least a second of said openings, said openings being located on a diameter of said ring.

9. A headphone cushion in accordance with claim 1 and further comprising at least a second ring separated by a groove between the first and second of said rings.

10. A headphone cushion in accordance with claim 5 and further comprising at least a second ring separated by a groove between the first and second of said rings.

11. A headphone cushion in accordance with claim 6 and further comprising at least a second ring separated by a groove between the first and second of said rings.

* * * * *

UNITED STATES PATENT AND TRADEMARK OFFICE
CERTIFICATE OF CORRECTION

PATENT NO. : 4,856,118

DATED : August 15, 1989

INVENTOR(S) : Roman Sapiejewski

It is certified that error appears in the above-identified patent and that said Letters Patent is hereby corrected as shown below:

Column 2, lines 40-41 - should read --material that behaves like an elastic solid capable of sustaining deformation without permanent loss of size, or shape and that--.

Signed and Sealed this

First Day of October, 1991

Attest:

Attesting Officer

HARRY F. MANBECK, JR.

Commissioner of Patents and Trademarks